United States Patent
Schmidlin et al.

(10) Patent No.: US 10,923,222 B2
(45) Date of Patent: Feb. 16, 2021

(54) SYSTEM FOR ADMINISTERING A PHARMACEUTICAL PRODUCT

(71) Applicant: Novartis AG, Basel (CH)

(72) Inventors: Alain Schmidlin, Basel (CH); Mario Iobbi, Basel (CH); Erich Studer, Basel (CH); Andrew Bryant, Basel (CH)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 16/493,729

(22) PCT Filed: Feb. 1, 2018

(86) PCT No.: PCT/EP2018/052541
§ 371 (c)(1),
(2) Date: Sep. 12, 2019

(87) PCT Pub. No.: WO2018/166702
PCT Pub. Date: Sep. 20, 2018

(65) Prior Publication Data
US 2020/0111556 A1    Apr. 9, 2020

Related U.S. Application Data

(60) Provisional application No. 62/471,380, filed on Mar. 15, 2017.

(30) Foreign Application Priority Data

Mar. 31, 2017  (EP) ..................................... 17164116

(51) Int. Cl.
*G16H 20/13* (2018.01)
*G16H 20/17* (2018.01)
(Continued)

(52) U.S. Cl.
CPC .............. *G16H 20/13* (2018.01); *A61M 5/24* (2013.01); *G16H 10/65* (2018.01); *G16H 20/17* (2018.01);
(Continued)

(58) Field of Classification Search
CPC ........ G16H 20/13; G16H 20/17; G16H 40/63; G16H 40/67; H04W 76/14; H04B 5/0031;
(Continued)

(56) References Cited

U.S. PATENT DOCUMENTS 3,583,399 A    6/1971  Ritsky
5,957,889 A    9/1999  Poulsen et al.
(Continued)

FOREIGN PATENT DOCUMENTS

EP    2249274 A1    11/2010
EP    2987517 A1    2/2016
(Continued)

OTHER PUBLICATIONS

"Using RFID to Track Critical Medical Device Information: Vizinex." Vizinex RFID, Jul. 7, 2015, (6 pages), https://web.archive.org/web/20150711212300/https://www.vizinexrfid.com/using-rfid-track-critical-medical-device-information/.
(Continued)

*Primary Examiner* — Pablo N Tran
(74) *Attorney, Agent, or Firm* — Moore & Van Allen, PLLC; Henry B. Ward, III

(57) ABSTRACT

The present disclosure relates to a system (100) for administering a pharmaceutical product. The system comprises a container (102) accommodating a pharmaceutical product. The container (102) comprises a wireless communication unit (112) and a memory (116) which stores an administration scheme specifically adapted to the pharmaceutical product accommodated in the container (102). The administra-
(Continued)

tion scheme specifies at least one administration-related parameter to be adhered to in administering the pharmaceutical product to a patient. The system further comprises a wireless communication device (104; 206; 208) configured to read the administration scheme from the memory (116) of the container (102) and to perform at least one action based on the administration scheme.

14 Claims, 4 Drawing Sheets

(51) Int. Cl.
*A61M 5/142* (2006.01)
*G16H 40/63* (2018.01)
*G16H 40/67* (2018.01)
*G16H 10/65* (2018.01)
*A61M 5/24* (2006.01)

(52) U.S. Cl.
CPC ............ *G16H 40/63* (2018.01); *G16H 40/67* (2018.01); *A61M 5/14248* (2013.01); *A61M 2205/3584* (2013.01); *A61M 2205/52* (2013.01)

(58) Field of Classification Search
CPC ........ A61M 5/142; A61M 39/10; A61M 5/14; A61M 5/14248; A61M 2205/3584; A61M 2205/52; A61M 5/24; G06F 19/00; G06K 19/077
See application file for complete search history.

(56) References Cited

U.S. PATENT DOCUMENTS

| | | | |
|---|---|---|---|
| 8,035,517 B2 | 10/2011 | Gibson | |
| 8,123,724 B2 | 2/2012 | Gillespie, III | |
| 8,308,457 B2* | 11/2012 | Rotem | A61M 5/14228 417/479 |
| 8,446,280 B2 | 5/2013 | Ortenzi et al. | |
| 8,475,409 B2* | 7/2013 | Tsoukalis | A61M 5/14224 604/131 |
| 9,424,020 B2* | 8/2016 | Borges | G06F 8/65 |
| 9,427,520 B2* | 8/2016 | Batch | G16H 10/60 |
| 9,452,267 B2 | 9/2016 | Reynolds et al. | |
| 9,750,896 B2* | 9/2017 | Kamen | A61M 5/14244 |
| 9,789,245 B2 | 10/2017 | Tieck et al. | |
| 9,949,642 B2* | 4/2018 | Love | A61B 5/002 |
| 10,010,273 B2* | 7/2018 | Sloan | G06F 19/00 |
| 10,137,246 B2* | 11/2018 | Estes | G06F 19/00 |
| 10,188,787 B2* | 1/2019 | Lanigan | A61M 5/1413 |
| 10,357,603 B2* | 7/2019 | Michaud | A61M 5/14248 |
| 10,380,321 B2* | 8/2019 | Kamen | G16H 20/17 |
| 10,384,001 B2* | 8/2019 | Nackaerts | G01F 13/006 |
| 10,453,157 B2* | 10/2019 | Kamen | G16H 40/67 |
| 2010/0160857 A1 | 6/2010 | Pongpairochana et al. | |
| 2011/0166512 A1 | 7/2011 | Both et al. | |
| 2011/0264033 A1 | 10/2011 | Jensen et al. | |
| 2011/0306929 A1 | 12/2011 | Levesque et al. | |
| 2013/0211330 A1 | 8/2013 | Pedersen et al. | |
| 2013/0225945 A1 | 8/2013 | Prince et al. | |
| 2014/0142507 A1 | 5/2014 | Armes | |
| 2015/0001285 A1 | 1/2015 | Halbert et al. | |
| 2015/0120321 A1* | 4/2015 | David | G16H 10/60 705/2 |
| 2015/0126926 A1 | 5/2015 | Giambattista et al. | |
| 2015/0246176 A1 | 9/2015 | Navarro et al. | |
| 2015/0310185 A1 | 10/2015 | Shah | |
| 2016/0015885 A1* | 1/2016 | Pananen | A61M 5/142 604/111 |
| 2016/0051750 A1 | 2/2016 | Tsoukalis | |
| 2016/0082182 A1 | 3/2016 | Gregory et al. | |
| 2016/0129182 A1* | 5/2016 | Schuster | A61M 5/16831 702/56 |
| 2016/0175515 A1 | 6/2016 | McCullough | |
| 2016/0260035 A1* | 9/2016 | Crooks | G06F 19/3456 |
| 2017/0143902 A1 | 5/2017 | Hansen et al. | |
| 2017/0258986 A1* | 9/2017 | Tsoukalis | A61M 5/14244 |
| 2017/0290974 A1* | 10/2017 | Tsoukalis | A61M 5/1407 |
| 2018/0318506 A1* | 11/2018 | Oakes | A61M 5/172 |
| 2019/0001057 A1* | 1/2019 | Tsoukalis | A61M 5/16895 |
| 2019/0175841 A1* | 6/2019 | Sjolund | A61B 5/7435 |
| 2019/0362832 A1* | 11/2019 | Bell | G07F 17/0092 |

FOREIGN PATENT DOCUMENTS

| | | |
|---|---|---|
| EP | 3106190 A1 | 12/2016 |
| FR | 2217026 A1 | 9/1974 |
| GB | 143084 A | 5/1920 |
| GB | 2145795 A | 4/1985 |
| WO | WO-2005072795 A2 | 8/2005 |
| WO | WO-2016033496 A1 | 3/2016 |

OTHER PUBLICATIONS

Center for Devices and Radiological Health. "Radio Frequency Wireless Technology in Medical Devices—Guidance." U.S. Food and Drug Administration, FDA, Aug. 14, 2013, (24 pages), https://www.fda.gov/regulatory-information/search-fda-guidance-documents/radio-frequency-wireless-technology-medical-devices-guidance-industry-and-fda-staff.

Fujitsu, "Application: Fujitsu RFID and Sensor Solution for Medical Device Traceability," https://www.fujitsu.com/us/Images/FUJITSU%20RFID%20for%20Medical%20Device%20Traceability.pdf, Aug. 2015, 2 pages.

International Search Report issued by the European Patent Office for International Patent Application No. PCT/EP2018/052541 dated Apr. 19, 2018.

Written opinion issued by the European Patent Office for International Patent Application No. PCT/EP2018/052541 dated Apr. 19, 2018.

International Preliminary Report on Patentability issued by the European Patent Office for International Patent Application No. PCT/EP2018/052541 dated Sep. 17, 2019.

\* cited by examiner

SYSTEM FOR ADMINISTERING A PHARMACEUTICAL PRODUCT

CROSS REFERENCE TO RELATED APPLICATIONS

This application is a national stage entry, filed under 35 U.S.C. 371, of International Application No. PCT/EP2018/052541, filed on Feb. 1, 2018, which claims the benefit of and priority to U.S. Provisional Application No. 62/471,380, filed on Mar. 15, 2017, and claims the benefit of and priority to European Patent Application No. 17164116.0, filed Mar. 31, 2017, the entire contents of which are hereby incorporated herein by reference in their entireties and for all purposes.

The present disclosure generally relates to the medical field. More particularly, the present disclosure relates to a system for administering a pharmaceutical product, a container accommodating a pharmaceutical product for use in the system as well as a medical device for use of the pharmaceutical product accommodated in the container.

In the medical field, it is well known to provide instructions for the use of a pharmaceutical product in the form of an instruction leaflet commonly supplied within the package in which the pharmaceutical product is sold. The instruction leaflet usually contains information about the pharmaceutical product, such as its field of application and its medical effects, as well as dosage instructions indicating the correct administration of the pharmaceutical product to a patient. Typically, the instruction leaflet is drafted in a general form applicable to a large number of patients so that specific usage instructions dedicated to a particular patient may still need to be provided in the form of separate prescription instructions prepared by a physician.

The adherence to the instructions given to a patient is typically in the responsibility of the patient itself and, therefore, the proper administration of a pharmaceutical product is generally dependent on the reliance and capability of the patient to strictly adhere to the instructions given. A patient's negligence may generally lead to improper administration of the pharmaceutical product and, hence, non-optimal achievement of the desired medical effects may be the consequence.

It is thus an object of the present disclosure to provide techniques that assist in improving the adherence of prescription instructions when administering a pharmaceutical product to a patient.

According to a first aspect, a system for administering a pharmaceutical product is provided. The system comprises a container accommodating a pharmaceutical product. The container comprises a wireless communication unit and a memory which stores an administration scheme specifically adapted to the pharmaceutical product accommodated in the container. The administration scheme specifies at least one administration-related parameter to be adhered to in administering the pharmaceutical product to a patient. The system further comprises a wireless communication device configured to read the administration scheme from the memory of the container and to perform at least one action based on the administration scheme.

The at least one administration-related parameter may relate to a prescription instruction directed to ensure proper administration of the pharmaceutical product to a patient. For example, the at least one administration-related parameter may be a parameter that corresponds to a general usage instruction for the pharmaceutical product applicable to every patient using the pharmaceutical product or to a specific usage instruction prescribed by a physician to a particular patient. For example, the at least one administration-related parameter may comprise at least one of a prescribed dosage of the pharmaceutical product, a prescribed date and/or time at which the pharmaceutical product is to be administered, a prescribed frequency and/or interval at which the pharmaceutical product is to be administered, a prescribed route of administration according to which the pharmaceutical product is to be administered, a prescribed location and/or geographical region at which the pharmaceutical product is to be administered, an identification of the patient to which the pharmaceutical product is to be administered, an identification of an administration device by which the pharmaceutical product is to be administered, and at least one control parameter for controlling a function specific to the administration device.

Among these parameters, the prescribed dosage of the pharmaceutical product may indicate the amount or volume (e.g., in units of ml, mg, etc.) of the pharmaceutical product to be administered, the prescribed frequency and/or interval may indicate the number of doses to be applied as well as a corresponding interval (e.g., hour, day, week, month, etc.) according to which the pharmaceutical product is to be administered, the prescribed route of administration may indicate the way through which the pharmaceutical product is to be administered to the body of the patient (e.g., oral, rectal, intra-arterial, intra-muscular, etc.), and the prescribed location may correspond to a particular treatment center at which the pharmaceutical product is to be administered, for example. The at least one administration-related parameter may be defined by the manufacturer of the pharmaceutical product and may be written to the memory of the container at an initial stage of the lifecycle of the pharmaceutical product and the container. The at least one administration-related parameter may also be written to the memory of the container at a later stage in the lifecycle of the pharmaceutical product, such as when the container is handed over to a patient in a pharmacy, for example.

The at least one administration-related parameter may be used by the wireless communication device (or a user thereof, e.g., the patient or a clinician) to verify that the pharmaceutical product is administered to the right patient, at the right time, at the right dosage and/or at the right location and, therefore, assist in ensuring that the given prescription instructions are strictly adhered to. If the wireless communication device is an administration device, the identification of the administration device may be used to verify that the pharmaceutical product is administered using the right device or the right type of device (e.g., syringe, automated injection device, patch pump device, etc.). In other words, the identification of the administration device may be used as a parameter to allow/disallow the pairing of the container with the administration device. The at least one control parameter for controlling a specific function of the administration device may enable the administration device to configure its own operation. In case of an automated injection device, the at least one control parameter may be used by the injection device to configure the injection speed of the pharmaceutical product from the container, for example.

The wireless communication unit of the container may be a passive wireless communication unit. In one variant, the wireless communication unit may be a Near Field Communication (NFC) unit and may comprise an RFID tag, for example. If the container comprises a label, the wireless communication unit and/or the memory may be included in the label. The wireless communication device may be an NFC enabled device which is configured to read the administration scheme from the memory of the container via NFC. It will be understood that other types of wireless communication technologies are conceivable for the same purpose. It is even conceivable that the wireless communication unit may be an active unit, given that corresponding power supply is provided. It will also be understood that the wireless communication device may not only read from the memory of the container, but may also write to the memory of the container, e.g., to set or update an administration-related parameter of the administration scheme stored in the memory.

In a simple example, the wireless communication device may be a smartphone having NFC functionality which may be employed by a user (e.g., the patient or a clinician) to read the administration scheme from the memory of the container. A dedicated application provided by the manufacturer of the pharmaceutical product may be installed on the smartphone in order to provide the required functionality to the smartphone. The at least one action performed by the wireless communication device may in such a case comprise outputting the administration scheme to a user for verification of the at least one administration-related parameter before administering the pharmaceutical product. Outputting the administration scheme may in one variant comprise displaying the administration scheme to the user (e.g., in text form), but may also comprise other types of output, such as audible outputs (e.g., narrative outputs or signal tones) or visual indications (e.g., using visual indicators, such as LEDs, provided at the wireless communication device).

In another example, the wireless communication device may be an administration device by which the pharmaceutical product may be administered from the container to the patient, such as a syringe which may accommodate the container and which may be used to inject the patient with the pharmaceutical product contained therein. In a variant, the administration device may be an automated administration device, i.e., an administration device which is configured to automatically administer (e.g., upon activation) the pharmaceutical product to the patient when the container is accommodated in or otherwise connected with the administration device. The at least one action performed by the wireless communication device may in this case comprise performing administration of the pharmaceutical product in accordance with the at least one administration-related parameter. An automated administration device may also verify the at least one administration-related parameter before administering the pharmaceutical product to the patient. If the verification of the at least one administration-related parameter fails (e.g., the right patient, the right time, the right dosage, the right location and/or the right device could not be confirmed), the administration device may refuse to perform the administration and may output a corresponding indication to the user. In one particular example, the wireless communication device may be an (e.g., automated) injection device, wherein performing the administration may comprise injecting the patient with the pharmaceutical product. The container may in this case be an injection cartridge, for example.

As described above, the identification of the administration device specified as a parameter of the administration scheme may be used to verify that the pharmaceutical product is administered using the right device or the right type of device. In a refinement of such variant, the container may be configured to interface with a plurality of types of administration devices for administering the pharmaceutical product from the container. In other words, the container may be a universal container which may be used in combination with different types of administration devices (e.g., syringe, automated injection device, patch pump device, etc.). For this purpose, the at least one administration-related parameter may comprise an identification of each type of administration device by which the pharmaceutical product may be administered from the container. For full compatibility with each type of administration device, the administration scheme may specify, for each of the plurality of types of administration devices, at least one control parameter for controlling a function specific to the respective type of administration device. Both the container and the respective administration devices may also be shape-coded so that the container may be accommodated in (or connected with) each of the respective administration devices in a form fitting manner.

It will be understood that what is said herein regarding the administration devices may also apply to other medical devices which are configured for use of the pharmaceutical product accommodated in the container, and not only to administration devices in particular. Thus, for example, more generally said, the wireless communication device may be a medical device, and performing the at least one action may comprise using the pharmaceutical product in accordance with the at least one administration-related parameter. Also, more generally said, the container may be configured to interface with a plurality of types of medical devices for use of the pharmaceutical product, wherein the administration scheme specifies, for each of the plurality of types of medical devices, at least one control parameter for controlling a function specific to the respective type of medical device. Such a medical device may be a reconstitution device, for example, which may be used for preparing a liquid or lyophilized solution for subsequent administration.

Once the pharmaceutical product (or a portion thereof) has been administered to the patient, usage-related information may be stored on the memory of the container in order to keep track of the administration performed. The memory of the container may thus further store usage-related information about the pharmaceutical product accommodated in the container, wherein the usage-related information may include at least one of a date of first use of the pharmaceutical product, a number of uses of the pharmaceutical product, and a remaining amount of the pharmaceutical product in the container. The wireless communication device may for this purpose be configured to write corresponding data to the memory of the container. If the wireless communication device is an administration device, the usage-related information may be written to the memory of the container upon completing an administration operation. For example, if an automated administration device has completed administering a portion of the pharmaceutical product from the container to the patient, the remaining volume of the pharmaceutical product left in the container may be written to the memory of the container so that the container is kept up-to-date regarding its fill volume. When the container is used the next time with the administration device (or another administration device), the respective administration device may verify if sufficient volume is available in the container to meet the prescribed dosage specified by the administration scheme, for example.

The memory of the container may further store non-administration-related information about the pharmaceutical product accommodated in the container. Non-administration-related information about the pharmaceutical product may be information which does not specifically relate to prescribed usage instructions for the pharmaceutical product, but which provides information about the product itself. For example, non-administration-related information about the pharmaceutical product may include at least one of a unique identification of the pharmaceutical product, a certificate of authenticity of the pharmaceutical product, at least one storage condition for the pharmaceutical product, an expiry date of the pharmaceutical product, an identification of a manufacturer of the pharmaceutical product, an identification of a physician who prescribed the pharmaceutical product, an identification of a distributor of the pharmaceutical product, and an identification of a batch in which the pharmaceutical product was produced.

Among this information, the unique identification of the pharmaceutical product may comprise a product name or another identifier uniquely identifying the pharmaceutical product. The certificate of authenticity may be used by the wireless communication device (or a user thereof, e.g., the patient or a clinician) to verify the genuineness of the pharmaceutical product and, as such, contribute to preventing fraud, tampering or counterfeiting with regard to the pharmaceutical product. The at least one storage condition for the pharmaceutical product may comprise indications regarding to the temperature (e.g., minimum/maximum temperature) and/or humidity (e.g., minimum/maximum humidity) at which the pharmaceutical product is to be stored. The manufacturer identification, the physician identification, the distributor (e.g., pharmacy or pharmacist) identification and the batch identification of the pharmaceutical product may be used to track the lifecycle of the container and may be used by the wireless communication device (or a user thereof, e.g., the patient or a clinician) to verify details about the pharmaceutical product accommodated in the container. The wireless communication device may further comprise one or more sensors (or may be configured to communicate with one or more remote sensors) in order to verify that the at least one storage condition is satisfied. To enable traceability of the container, the memory of the container may further store a unique identifier for the container.

The memory of the container may also store at least one file containing additional information about the pharmaceutical product and/or a link to a website providing additional information about the pharmaceutical product. The at least one file may comprise a document (e.g., a PDF document) or a multimedia file (e.g., a movie file), for example. The website may contain information about the pharmaceutical product which is not stored (or cannot be stored due to memory limitations) in the memory of the container itself. For example, the at least one file and/or the website may provide a more detailed product description, e.g., including illustrative images of the product, more detailed usage and prescription instructions (e.g., using illustrative movies), detailed information about the manufacturer, or the like.

In order to provide improved data security, the administration scheme may be stored in the memory of the container in an access protected manner. In one such variant, access to the administration scheme may be password protected. Thus, if a user (e.g., the patient or a clinician) wants to read the administration scheme from the memory of the container, the user may be prompted to enter a password at the wireless communication device. Additionally or alternatively, the administration scheme may be encrypted in the memory of the container and the wireless communication device may have a decryption key for decrypting the administration scheme. For example, if the wireless communication device is a smartphone, a dedicated application (e.g., provided by the manufacturer of the pharmaceutical product) holding the required decryption key may be installed on the smartphone. In a further variant, only selected portions of the administration scheme may be access protected. Access protection may be defined differently for read and write operations. It will be understood, that equivalent access protection may also be provided for the usage-related information and the non-administration-related information stored in the memory of the container.

In a refinement of the system, the system may further comprise a remote server. The wireless communication device may be configured to communicate with the remote server via wireless communication, preferably WLAN or Bluetooth communication. The remote server may reside in a cloud computing environment, for example, and may be accessible by the wireless communication device through the Internet. Communication between the wireless communication device and the remote server may be secured, e.g., using security protocols such as SSL, TLS, or the like.

The remote server may be used to implement various supplemental services associated with the administration of the pharmaceutical product. In one such variant, the remote server may host supplementary administration-related information accessible by the wireless communication device. For example, the remote server may store additional administration-related parameters which are not stored (or cannot be stored due to memory limitations) in the memory of the container itself. If the wireless communication device is an administration device, the administration device may download one or more additional administration-related parameters from the remote server and apply these parameters when performing administration of the pharmaceutical product accordingly.

Further, the wireless communication device may be configured to exchange at least part of the data stored in the memory of the container with the remote server. In one variant, the wireless communication device may replicate the data stored on the memory of the container (or parts thereof) on the remote server. The exchanged data may be used by the remote server to provide additional services to a user (e.g., the patient or a clinician). For example, the remote server may be configured to notify, based on an analysis of the data stored on the remote server, a user of an upcoming administration to be performed according to the administration scheme. Such notifications may be transmitted in the form of reminders or alarms to a user's end device, such as to the user's pager or smartphone. In another example, the remote server may be configured to report a status relating to the container and/or the wireless communication device upon request by the user. Such report may allow the user to check the status of an ongoing administration, to check the result of a completed administration, to track a therapy session, or to track the entire adherence history, for example. The data stored in the remote server may also be aggregated and shared with a caregiver or healthcare provider (HCP). In another example, the data in the remote server may be stored in an electronic patient record. In an electronic patient record, further patient-related information may be stored, such as other drugs prescribed to the patient, for example. Based on the information stored in the electronic patient record, it is generally conceivable to perform an analysis and generate an alert, if one or more drugs prescribed to the patient are incompatible, for example.

In a further variant, the wireless communication device may be instructed by the remote server to write data to the memory of the container, e.g., in order to update at least one administration-related parameter of the administration scheme or to update other data stored in the memory of the container. As an example, if it is encountered that a batch in which the pharmaceutical product was produced has been recalled due to a production fault, the remote server may instruct the wireless communication device to write data into the memory of the container marking the container as unusable so as to prevent further use of the container. The requirement for recalling the container may be identified through the batch identification stored in the memory of the container or the remote server, respectively. If the wireless communication device is an administration device, the administration device may be configured to verify if the container is marked as unusable and block any administration of the pharmaceutical product from the container accordingly.

According to a second aspect, a container accommodating a pharmaceutical product is provided. The container comprises a wireless communication unit and a memory which stores an administration scheme specifically adapted to the pharmaceutical product accommodated in the container. The administration scheme specifies at least one administration-related parameter to be adhered to in administering the pharmaceutical product to a patient.

According to a third aspect, a medical device for use of a pharmaceutical product accommodated in a container is provided. The container comprises a wireless communication unit and a memory which stores an administration scheme specifically adapted to the pharmaceutical product accommodated in the container. The administration scheme specifies at least one administration-related parameter to be adhered to in administering the pharmaceutical product to a patient. The medical device is enabled for wireless communication with the wireless communication unit of the container. The medical device is further configured to read the administration scheme from the memory of the container and to use the pharmaceutical product in accordance with the at least one administration-related parameter.

Both the container according to the second aspect and the medical device according to the third aspect may correspond to the container and the medical device, in particular the administration device, described above in relation to the system according to the first aspect. All features described above for the container and the medical device, in particular the administration device, may apply to the container according to the second aspect and the medical device according to the third aspect as well. Unnecessary repetitions are thus omitted.

In the following, the present disclosure will further be described with reference to exemplary implementations illustrated in the figures, in which.

Figure 1:
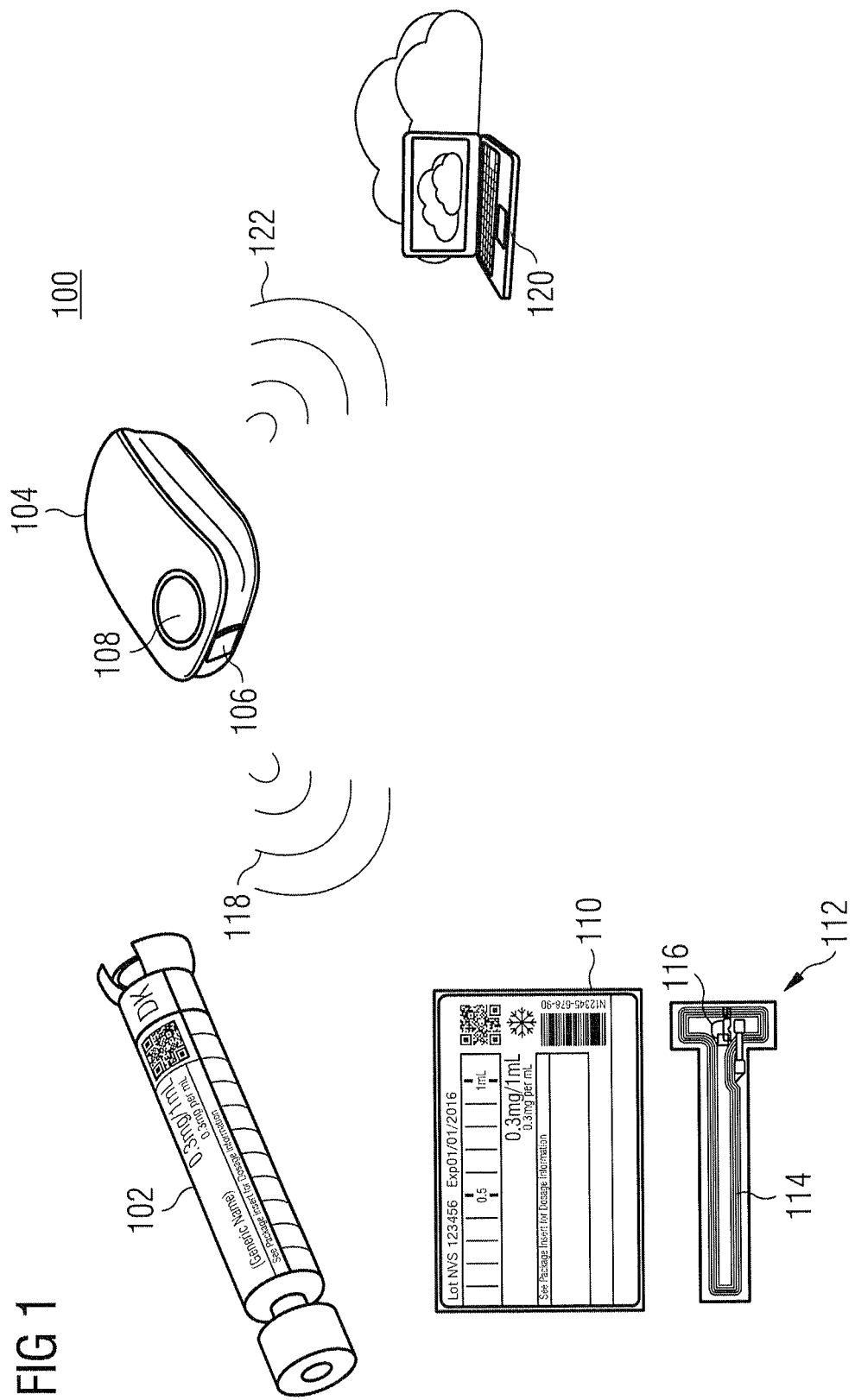
FIG. 1 illustrates an exemplary system comprising a container accommodating a pharmaceutical product, a corresponding administration device and a remote server according to the present disclosure.
Figure 3:
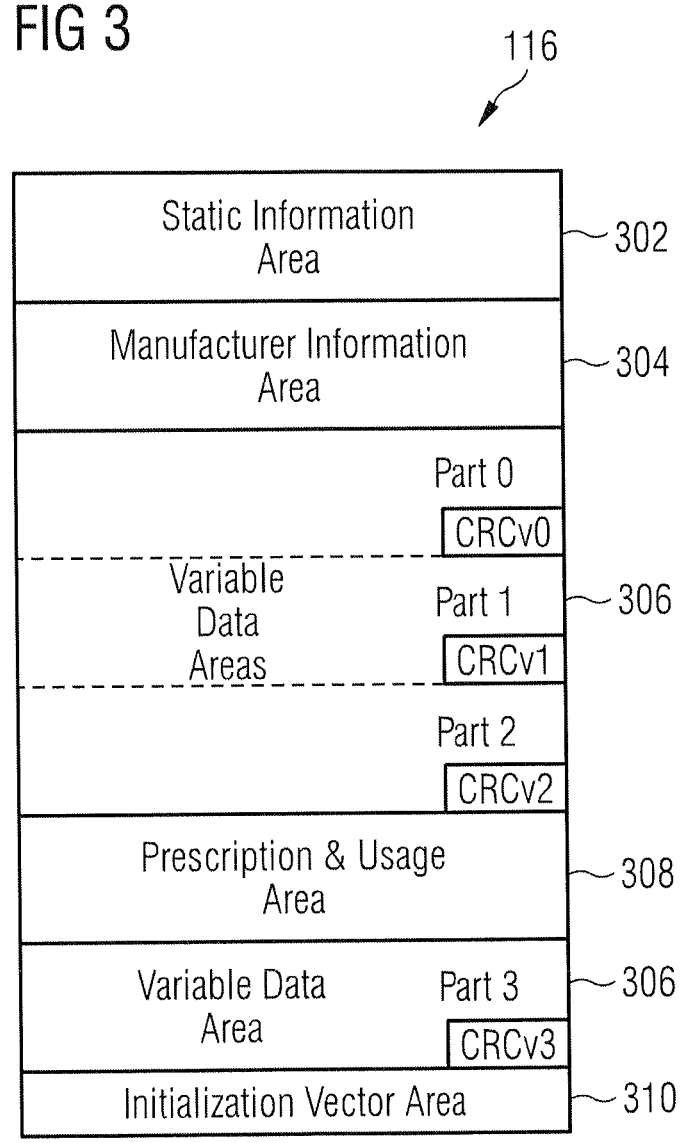
Figure 4:
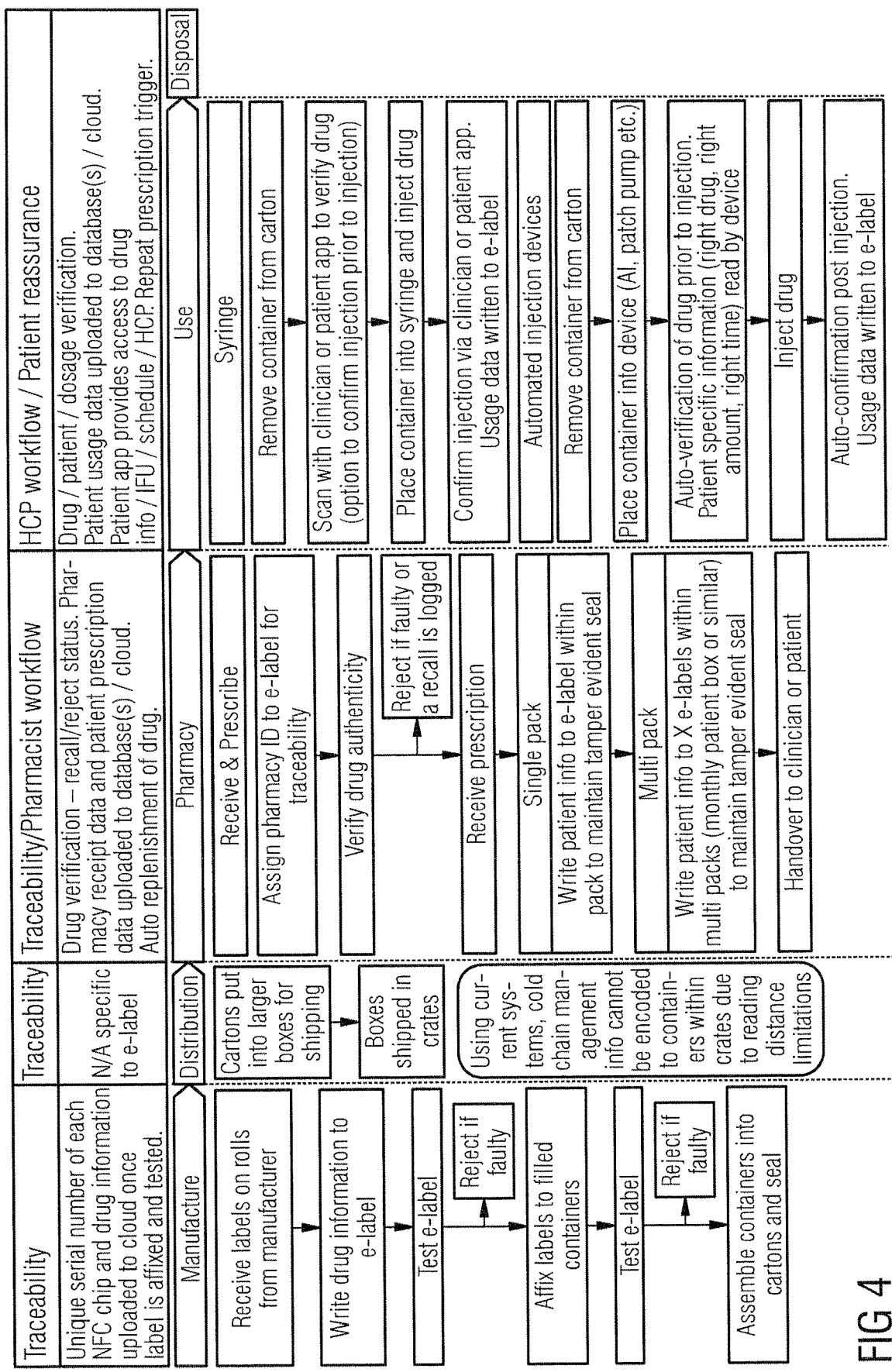

FIG. 3 schematically illustrates an exemplary memory structure of a memory of the container of FIG. 1; and FIG. 4 illustrates an exemplary lifecycle of the container of FIG. 1 from manufacture to disposal.

In the following description, for purposes of explanation and not limitation, specific details are set forth in order to provide a thorough understanding of the present disclosure. It will be apparent to one skilled in the art that the present disclosure may be practiced in other implementations that depart from these specific details.

FIG. 1 illustrates an exemplary system 100 for administering a pharmaceutical product to a patient according to the present disclosure. The system 100 comprises a container 102 which accommodates the pharmaceutical product as well as an administration device 104 for administering the pharmaceutical product accommodated in the container 102 to a patient. In the illustrated example, the administration device 104 is provided as an automated injection device and the container 102 is provided as an injection cartridge which accommodates the pharmaceutical product in liquid form and which has a shape-coded cylindrical form so that it may be placed into a slide-in module 106 of the administration device 104 in a form fitting manner. When the container 102 is placed into the slide-in module 106 and slid into the administration device 104 (as shown in FIG. 1), the administration device 104 may automatically dispense the pharmaceutical product from the container 102 and thereby administer the pharmaceutical product to the patient. The administration device 104 may comprise a drive mechanism for this purpose which may be configured to extend an injection needle to the outside of the device (for example at the bottom side of the administration device 104, not shown) through which the pharmaceutical product may be injected into the body of the patient. The drive mechanism may be activated by pressing a button 108 of the administration device 104 when the bottom side of the administration device 104 lies flat against the body of the patient, for example.

The container 102 comprises a printed label 110 which is affixed around the outer circumference of the container 102 and which presents information about the pharmaceutical product accommodated in the container 102 (e.g., product name, batch number, expiry date, etc.). FIG. 1 shows an exemplary label 110 for illustrative purposes additionally in an un-affixed and unwound form below the container 102. The label 110 comprises a Near Field Communication (NFC) unit 112 having an RFID antenna 114 which is integrated into the sheet of the label 110 so that it is not visible from the outside. For illustrative purposes, the NFC unit 112 is shown in FIG. 1 below the label 110 in a detached form. The NFC unit 112 comprises a memory 116 in which an administration scheme that is specifically adapted to the pharmaceutical product accommodated in the container 102 is stored. As described above, the administration scheme may specify at least one administration-related parameter to be adhered to in administering the pharmaceutical product to the patient.

The administration device 104 comprises an NFC enabled interface and is enabled for communication with the NFC unit 112 using NFC (indicated by reference numeral 118). When the container 102 is inserted into the administration device 104, the administration device 104 may read the administration scheme from the memory 116 via NFC and take into consideration the at least one administration-related parameter specified by the administration scheme for the automated administration of the pharmaceutical product to the patient. For example, when button 108 of the administration device 104 is pressed, the administration device 104 may check the identification of the patient, the prescribed date/time, the prescribed location and/or the identification of the administration device specified by the administration scheme in order to verify that the pharmaceutical product is administered to the right patient, at the right time, at the right location and/or using the right device. If the verification is successful, the administration device 104 may perform the administration of the pharmaceutical product in accordance with further administration-related parameters specified by the administration scheme, such as the prescribed dosage and/or the injection speed indicated by an administration device specific control parameter. If the verification is not successful, on the other hand, the administration device 104 may refuse to perform administration of the pharmaceutical product and output a corresponding indication to the patient.

Once the pharmaceutical product (or a portion thereof) has been administered to the patient, the administration device 104 may write usage-related information to the memory 116 of the container 102 in order to keep track of the administration performed. For example, if the container 102 was used for the first time, the administration device 104 may set the date of first use in the memory 116. Otherwise, the administration device 104 may update the number of uses of the pharmaceutical product in the memory 116. The administration device 104 may also update the remaining fill volume of the pharmaceutical product in the container 102 so that, when the container 102 is used the next time with the administration device 104 (or another administration device), the respective administration device may verify if sufficient fill volume is available in the container 102 to meet the prescribed dosage specified by the administration scheme before performing the next administration. Further, the usage-related information may not only be used to keep track of the administration performed but, since this information generally indicates that the container 102 has been used, it may also be used to prevent illegal container refilling by checking by the administration device 104, before an administration is performed, whether an (apparently) fully filled container has already been used or not. In a further example, usage-related information may also be stored on a memory of the administration device 104 itself in order to support partial dosing using several containers. For example, if a remaining fill volume of the pharmaceutical product in the container 102 is not sufficient to meet the prescribed dosage according to the administration scheme, the remaining fill volume may be administered, in a first administration step, from the container 102 and a value indicative of the remaining required volume to be administered to meet the prescribed dosage may be stored on the administration device 104. The container 102 may then be replaced by a fresh (e.g., fully filled) container from which the remaining required volume may then be administered by the administration device 104 in a second administration step.

As described above, in addition to the administration scheme and the usage-related information about the pharmaceutical product, the memory 116 of the container 102 may further store non-administration-related information about the pharmaceutical product and/or a file or a link to a website providing additional information about the pharmaceutical product.

As may be seen in FIG. 1, the system 100 also comprises a remote server 120 which is exemplarily illustrated by a personal/laptop computer in FIG. 1. It will be understood that any other type of computing system may be employed for the remote server 120, such as a physical or virtual server computer which may reside in a cloud computing environment, or even a smartphone, for example. Besides the NFC enabled interface, the administration device 104 also comprises a wireless communication interface and is thus enabled to communicate with the remote server 120 using wireless communication (indicated by reference numeral 122), preferably WLAN or Bluetooth. The administration device 104 may access the remote server 120 through the Internet. The communication between the administration device 104 and the remote server 120 may be secured, e.g., using security protocols such as SSL, TLS, or the like. Also, it will be understood that the administration device 104 may communicate with the remote server 120 via an intermediate device. For example, the intermediate device may be a personal computer, a laptop computer or a smartphone (e.g., of a clinician or the patient) which may communicate with the administration device 104, on the one hand, and which may communicate with the remote server 120 (e.g., a server residing in a cloud computing environment), on the other hand.

The remote server 120 may be used to implement various supplemental services associated with the administration of the pharmaceutical product. For example, the remote server may host supplementary administration-related information accessible by the administration device 104, such as additional administration-related parameters which are not stored (or cannot be stored due to memory limitations) in the memory 116 of the container 102. The administration device may download the additional administration-related parameters from the remote server 120 and apply these parameters when performing administration of the pharmaceutical product accordingly. The administration device 104 may also exchange at least part of the data stored in the memory 116 with the remote server 120. For example, the administration device 104 may replicate the data stored on the memory 116 (or parts thereof) on the remote server 120. The exchanged data may be used by the remote server 120 to provide additional services to a user (e.g., the patient or a clinician). In an example, the remote server 120 may notify, based on an analysis of the exchanged or replicated data, a user of an upcoming administration to be performed according to the administration scheme. Such notifications may be transmitted in the form of reminders or alarms to a user's pager or smartphone, for example. In another example, the remote server 120 may report a status relating to the container 102 and/or the administration device 104 upon request by the user. Such report may allow the user to check the status of an ongoing administration, to check the result of a completed administration, to track a therapy session, or to track the entire adherence history, for example. The data stored in the remote server 120 may also be aggregated and shared with a caregiver or HCP. In another example, the data in the remote server 120 may be stored in an electronic patient record. In an electronic patient record, further patient-related information may be stored, such as other drugs prescribed to the patient, for example. Based on the information stored in the electronic patient record, it is generally conceivable to perform an analysis and generate an alert, if one or more drugs prescribed to the patient are incompatible, for example.

The remote server 120 may further instruct the administration device 104 to write data to the memory 116, e.g., in order to update at least one administration-related parameter of the administration scheme or to write other data to the memory 116. As an example, if it is encountered that a batch in which the pharmaceutical product was produced has been recalled due to a production fault, the remote server 120 may instruct administration device 104 to write data into the memory 116 of the container 102 marking the container 102 as unusable so as to prevent further use of the container 102. The requirement for recalling the container 102 may be identified through the batch identification stored in the memory 116 or in the remote server 120, respectively. Before performing administration of the pharmaceutical product, the administration device 104 may verify if the container 102 is marked as unusable and block any administration of the pharmaceutical product from the container 102 accordingly.

It will be understood that the above description of the system 100 is merely exemplary and that various other implementations in accordance with the present disclosure are conceivable. For example, the pharmaceutical product does not necessarily have to be provided in liquid form and the container does not necessarily have to be a cylindrical injection cartridge. It will be understood that the principles of the present disclosure may be practiced with any other suitable form of pharmaceutical product and corresponding container, such as with tablets provided in another type of suitable packaging, for example. It will also be understood that the NFC unit of the container does not necessarily have to be provided with a label affixed to the container, but may be integrated into the container itself, for example. The skilled person will further appreciate that other types of passive wireless communication technologies (i.e., other than NFC) may be used to realize the communication between the administration device and the container. If corresponding power supply is available, the wireless communication unit of the container may even be provided as an active unit.

Moreover, it will be understood that other types of wireless communication devices (i.e., other than the automated injection device 104) may be used to read and write data from and to the memory of the container. For example, the wireless communication device may be a smartphone having required functionality (e.g., NFC functionality) to communicate with the wireless communication unit of the container and to read and/or write data from and to the memory. The smartphone may have a dedicated application (e.g., provided by the manufacturer of the pharmaceutical product) installed in order to provide the required functionality. The smartphone may be used to read the administration scheme from the container for verification by a user (e.g., the patient or a clinician) or to read other data from the memory of the container, such as non-administration-related information like the certificate of authenticity of the pharmaceutical product in order to verify the genuineness of the pharmaceutical product.

In another example, the wireless communication device may be a non-automated administration device, such as a manually operable syringe. Similar to the automated administration device 104, a non-automated administration device may verify that the pharmaceutical product is administered to the right patient, at the right time, at the right location and/or using the right device, for example. The non-automated administration device may output a corresponding indication for the result of the verification, e.g., via text form on a display, through an audible output, or through visual indicators, such as LEDs provided at the housing of the device.

It will further be understood that, similar to the remote server 120, the administration device 104 (or another type of administration device) may be configured to communicate via wireless communication 122 with end-user devices, such as with a user's laptop or smartphone. These devices may have a dedicated application (e.g., provided by the manufacturer of the administration device) installed enabling the user to configure or view a status of the respective administration device, for example.

Figure 2:
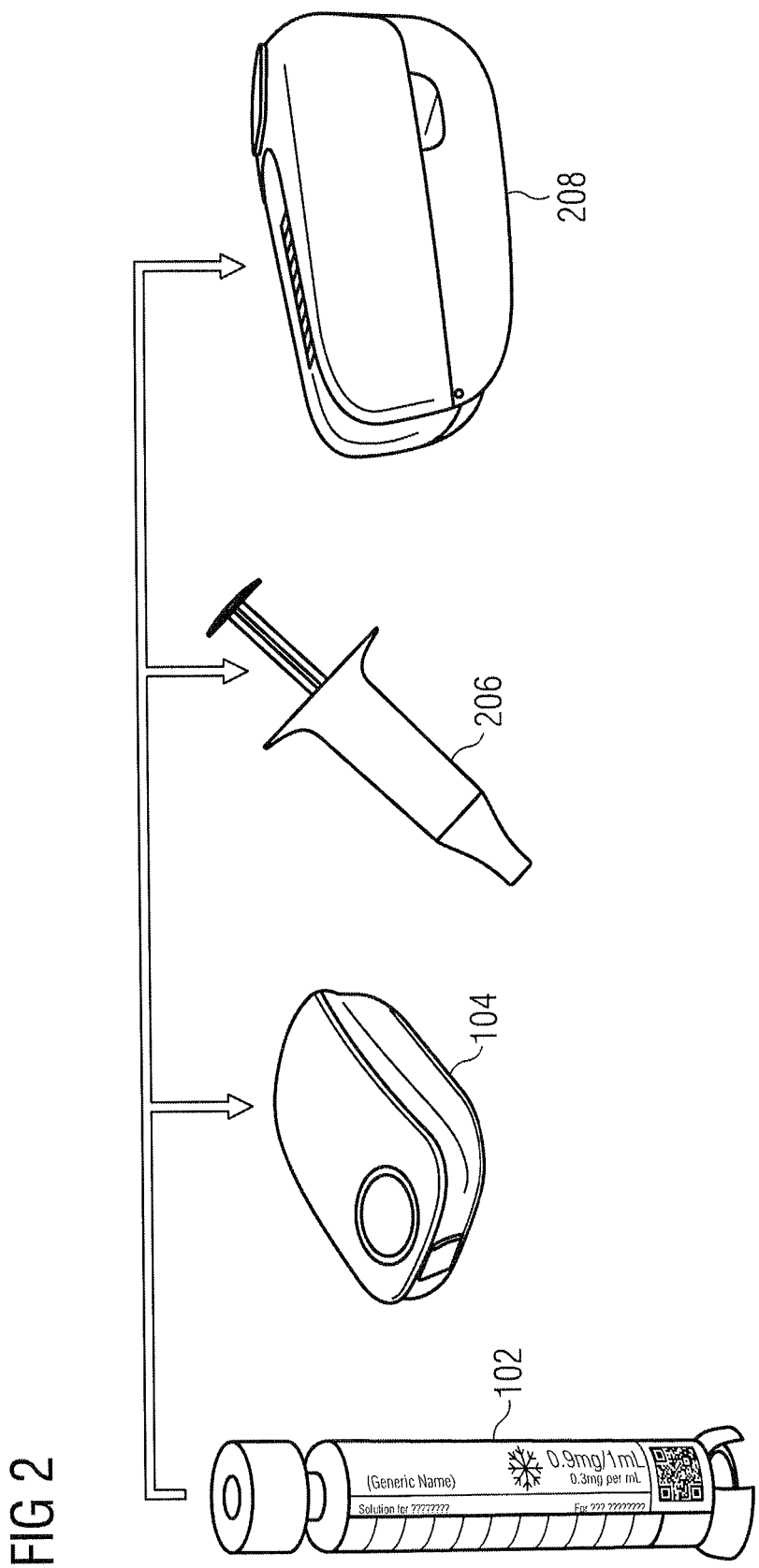
FIG. 2 illustrates that the container of FIG. 1 may interface with a plurality of types of administration devices.

FIG. 2 is an illustration which shows that the container 102 may be configured to interface with a plurality of types of administration devices. The container 102 may thus be a universal container which may be used in combination with different types of administration devices. As depicted in the example of FIG. 2, the container 102 may not only be used with the automated injection device 104, but also in combination with a manually operable (i.e., non-automated) syringe 206 as well as an automated patch pump device 208. For full compatibility with each of these devices, the administration scheme stored in the memory 116 of the container 102 may comprise an identification of each of these devices so that, once the container 102 is inserted into the respective device, the respective device may verify that the container 102 is inserted into the right device. The respective device may output a result of the verification accordingly and, in case of a negative verification, block administration of the pharmaceutical product from the container 102. For the automated administration devices, the administration scheme stored in the memory 116 may further comprise control parameters for controlling functions specific to these devices. For example, in case of the automated injection device 104, a control parameter specified in the administration scheme may be used to configure the injection speed of the pharmaceutical product from the container 102. Each of the administration devices 104, 206 and 208 may have a receiving portion which may receive the container 102. The container 102 and the respective receiving portions may be shape-coded so that the container 102 may be accommodated in the receiving portions in a form fitting manner. It will be understood that the container 102 may not only be configured to interface with the types of administration devices illustrated in FIG. 2, but also with other types of medical devices, such as with reconstitution devices, for example, which may be used for preparing a liquid or lyophilized solution for subsequent administration.

FIG. 3 schematically illustrates an exemplary memory structure of the memory 116 of the container 102. As shown, the memory 116 may comprise five different types of memory areas: a static information area 302, a manufacturer information area 304, variable data areas 306, a prescription and usage area 308, and an initialization vector area 310. Among these types, the static information area 302 may be used to store unmodifiable information which may be written during manufacture and which may be write protected thereafter. This information may include the batch identification, the expiry date or the storage conditions (e.g., storage temperature/humidity) of the pharmaceutical product, for example. The manufacturer information area 304 may be used to store information which may be readable by off-the-shelf NFC enabled devices, such as NFC enabled smartphones, to allow users to identify information about the manufacturer and the pharmaceutical product without the need to use proprietary reading equipment. Information stored in the manufacturer information area 304 may include the manufacturer identification, the unique product identification or the file or link to the website providing additional information about the pharmaceutical product, for example. The information in this area may be stored in ASCII format in order to ensure its readability by off-the-shelf devices. The variable data areas 306 may be used to store miscellaneous information that may differ dependent on the pharmaceutical product accommodated in the container 102. The information stored in this area may not have a pre-defined format and a fixed location or length. Information stored in this area may include the identification of the administration device or control parameters for controlling a function specific to the administration device. The prescription and usage area 308 may be used to store information relevant to the prescription and usage of the pharmaceutical product. Such information may include the prescribed dosage, the prescribed date and/or time, the patient identification, the number of uses or the remaining fill volume of the container 102, for example. Finally, the initialization vector area 310 may contain information used for encryption and decryption.

Each of the memory areas may be assigned with a dedicated level of read and/or write access to implement desired access protection. For example, the static information area 302 and the manufacturer information area 304 may be freely readable, but writable by the manufacturer of the pharmaceutical product only. The variable data areas 306, the prescription and usage area 308 and the initialization vector area 310, on the other hand, may be writable by a physician or a pharmacy, but their readability may generally be restricted. Read protection may be realized by password protection, for example. Additionally or alternatively, read protection may be realized by encrypting the information stored in the respective memory areas so that only a wireless communication device which holds the required decryption key may read from the respective memory areas.

FIG. 4 illustrates an exemplary lifecycle of the container 102. In FIG. 4, the terms "e-label", "drug" and "cloud" correspond to the terms "label", "pharmaceutical product" and "remote server" described above, respectively. The lifecycle may comprise the stages manufacture, distribution, pharmacy, use and disposal.

In the manufacture stage, initial information about the pharmaceutical product may be written to the memory 116 of the label 110 by the manufacturer of the pharmaceutical product (e.g., into the static and manufacturer information areas 302 and 304, as described above). The label 110 may then be affixed to the container 102 which may be prefilled with the pharmaceutical product. Tests on the NFC functionality of the label 110 may be performed before and after the affixation. Once the label 110 is successfully tested, the unique label identifier (e.g., the unique serial number of the NFC unit 112) as well as the information about the pharmaceutical product may be uploaded to the remote server 120 to ensure traceability of the container 102 and the pharmaceutical product. The container 102 may then be assembled together with other containers into a carton for distribution and sealed. In the distribution stage, the carton may be placed into a box and shipped.

In the subsequent stage, a pharmacy (or another distribution center) may receive the container 102 and write distributor identification (e.g., a pharmacy ID) to the memory 116 of the label 110 for further traceability of the container 102. Also, the pharmacy may verify the genuineness of the pharmaceutical product by checking the certificate of authenticity stored in the memory 116 of the label 110. If the verification fails, the container 102 may be marked as unusable by writing corresponding data into the memory 116 of the label 110. Further, the pharmacy may receive a patient specific prescription from a physicist and write the corresponding prescription instructions to the memory 116 of the label 110 so that the administration scheme stored in the memory 116 of the label 110 properly reflects the received prescription instructions. The data written to the memory 116 may again be uploaded to the remote server 120 and the container 102 may then be handed over to the patient or a clinician, for example.

The use stage may differ depending on which type of administration device is used for administering the pharmaceutical product from the container 102 to the patient. If a manual syringe which is not enabled for wireless communication is used, the label 110 of the container 102 may be scanned by an NFC enabled device (e.g., by a smartphone having an application provided by the manufacturer) in order to verify that the pharmaceutical product is administered to the right patient, at the right time and/or at the right location, for example. Upon completion of the injection using the syringe, the NFC enabled device may be used to write usage-related information to the memory 116 of the label 110. If, on the other hand, an automated injection device (like the automated injection device 104) is used, the container 102 may be placed into the device and the device may perform (e.g., upon activation) an automated verification of the pharmaceutical product before administering it to the patient. If the verification is successful, the device may perform automated administration of the pharmaceutical product and, upon completion, the device write usage-related information to the memory 116 of the label 110. The usage-related information may also be uploaded to the remote server 120 to keep track of the usage of the container 102. Finally, if the pharmaceutical product has been partly or fully dispensed and the container 102 is no longer usable, the container 102 may be disposed.

It is believed that the advantages of the technique presented herein will be fully understood from the foregoing description, and it will be apparent that various changes may be made in the form, constructions and arrangement of the exemplary aspects thereof without departing from the scope of the disclosure or without sacrificing all of its advantageous effects. Because the technique presented herein can be varied in many ways, it will be recognized that the disclosure should be limited only by the scope of the claims that follow.

The invention claimed is:

1. A system for administering a pharmaceutical product, comprising:
    a container accommodating a pharmaceutical product, the container comprising a wireless communication unit and a memory which stores an administration scheme specifically adapted to the pharmaceutical product accommodated in the container, the administration scheme specifying at least one administration-related parameter to be adhered to in administering the pharmaceutical product to a patient;
    a wireless communication device configured to read the administration scheme from the memory of the container and to replicate the administration scheme, including information about the pharmaceutical product, on a remote server; and
    a remote server configured to (i) store patient-related information including medications prescribed to the patient in an electronic patient record, (ii) perform, based on the patient-related information stored in the electronic patient record, an analysis, (iii) generate an alert in response to the pharmaceutical product and one or more of other medications prescribed to the patient being incompatible, and (iv) instruct the wireless communication device to write data into the memory of the container marking the container as unusable so as to prevent further use of the container,
    wherein the wireless communication device is configured to communicate with the remote server via wireless communication.

2. The system of claim 1, wherein the at least one administration-related parameter comprises at least one of:
    a prescribed dosage of the pharmaceutical product,
    a prescribed date and/or time at which the pharmaceutical product is to be administered, a prescribed frequency and/or interval at which the pharmaceutical product is to be administered, a prescribed route of administration according to which the pharmaceutical product is to be administered, a prescribed location and/or geographical region at which the pharmaceutical product is to be administered, an identification of the patient to which the pharmaceutical product is to be administered, an identification of an administration device by which the pharmaceutical product is to be administered, and at least one control parameter for controlling a function specific to the administration device.

3. The system of claim 1, wherein the wireless communication unit of the container is a Near Field Communication (NFC) unit, and at least one selected from the group comprising:

wherein the wireless communication device is an NFC enabled device configured to read the administration scheme from the memory of the container via NFC, and wherein the container comprises a label, and wherein the wireless communication unit and the memory are included in the label.

4. The system of claim 1, wherein performing the at least one action comprises outputting the administration scheme to a user for verification of the at least one administration-related parameter before administering the pharmaceutical product.

5. The system of claim 1, wherein the wireless communication device is an administration device, and wherein performing the at least one action comprises performing administration of the pharmaceutical product in accordance with the at least one administration-related parameter, and wherein the administration device is an injection device, and wherein performing the administration comprises injecting the patient with the pharmaceutical product.

6. The system of claim 1, wherein the container is configured to interface with a plurality of types of medical devices for use of the pharmaceutical product, and wherein the administration scheme specifies, for each of the plurality of types of medical devices, at least one control parameter for controlling a function specific to the respective type of medical device.

7. The system of claim 1, wherein the memory of the container further stores usage-related information about the pharmaceutical product accommodated in the container, the usage-related information including at least one of:

a date of first use of the pharmaceutical product, a number of uses of the pharmaceutical product, and a remaining amount of the pharmaceutical product in the container.

8. The system of claim 1, wherein the memory of the container further stores non-administration-related information about the pharmaceutical product accommodated in the container, the non-administration-related information including at least one of:

a unique identification of the pharmaceutical product, a certificate of authenticity of the pharmaceutical product, at least one storage condition for the pharmaceutical product, an expiry date of the pharmaceutical product, an identification of a manufacturer of the pharmaceutical product, an identification of a physician who prescribed the pharmaceutical product, an identification of a distributor of the pharmaceutical product, and an identification of a batch in which the pharmaceutical product was produced.

9. The system of claim 1, wherein the memory of the container further stores at least one selected from the group comprising (1) at least one file containing additional information about the pharmaceutical product and (2) a link to a website providing additional information about the pharmaceutical product.

10. The system of claim 1, wherein the administration scheme is stored in the memory of the container in an access protected manner.

11. The system of claim 10, wherein access to the administration scheme is password protected, and/or wherein the administration scheme is encrypted in the memory of the container and the wireless communication device has a decryption key for decrypting the administration scheme.

12. The system of claim 1, wherein the wireless communication comprises at least one selected from the group consisting of Wireless Local Area Network (WLAN) and Bluetooth® communication.

13. The system of claim 12, further comprising at least one selected from the group comprising:

wherein the remote server hosts supplementary administration-related information accessible by the wireless communication device, wherein the wireless communication device is configured to exchange at least part of the data stored in the memory of the container with the remote server, wherein the remote server is configured to notify a user of an upcoming administration to be performed according to the administration scheme, and wherein the remote server is configured to report a status relating to the container and/or the wireless communication device upon request by a user.

14. The system of claim 1, further comprising a medical device for use of the pharmaceutical product accommodated in the container, wherein the medical device is enabled for wireless communication with the wireless communication unit of the container, and wherein the medical device is configured to read the administration scheme from the memory of the container and to use the pharmaceutical product in accordance with the at least one administration-related parameter.

* * * * *